US011193795B2

(12) United States Patent
Foster et al.

(10) Patent No.: US 11,193,795 B2
(45) Date of Patent: Dec. 7, 2021

(54) ELECTROMAGNETIC TRACKING SYSTEM USING ROTATING FIELDS GENERATED FROM A RADIAL ARRANGEMENT OF TRANSMITTERS IN A HOUSING

(71) Applicant: Boston Scientific Scimed Inc., Maple Grove, MN (US)

(72) Inventors: Daniel J. Foster, Lino Lakes, MN (US); Matthew Hein, Eden Prairie, MN (US); Roger N. Hastings, Maple Grove, MN (US)

(73) Assignee: Boston Scientific Scimed, Inc, Maple Grove, MN (US)

( * ) Notice: Subject to any disclaimer, the term of this patent is extended or adjusted under 35 U.S.C. 154(b) by 598 days.

(21) Appl. No.: 15/998,593

(22) Filed: Aug. 16, 2018

(65) Prior Publication Data

US 2019/0056242 A1    Feb. 21, 2019

Related U.S. Application Data

(60) Provisional application No. 62/546,532, filed on Aug. 16, 2017.

(51) Int. Cl.
*G01D 5/20* (2006.01)
*A61B 5/06* (2006.01)
(Continued)

(52) U.S. Cl.
CPC ............. *G01D 5/204* (2013.01); *A61B 5/062* (2013.01); *G01D 5/16* (2013.01); *A61B 5/686* (2013.01);
(Continued)

(58) Field of Classification Search
CPC . A61B 1/00158; A61B 1/041; A61B 1/00016; A61B 5/062; A61B 2034/2051; A61B 34/20; A61B 5/073; A61B 8/12
See application file for complete search history.

(56) References Cited

U.S. PATENT DOCUMENTS 5,347,289 A     9/1994   Elhardt
5,425,367 A     6/1995   Shapiro et al.
(Continued)

FOREIGN PATENT DOCUMENTS

EP         1174082 A1      1/2002

OTHER PUBLICATIONS

Hastings, R. (2014). Rotating magnet localization of medical devices. IEEE, Engineering in Medicine Biology Society, Santa Clara Valley Chapter, Calendar Year 2014 Presentations, pp. 4-5, retrieved from http://www.ewh.ieee.org/r6/scv/embs/pages/2014.html.
(Continued)

*Primary Examiner* — Jason M Ip
(74) *Attorney, Agent, or Firm* — Faegre Drinker Biddle & Reath LLP (57) ABSTRACT

A system comprises first and second rotating magnetic field transmitter assemblies positioned in a planar arrangement. The first and second rotating magnetic field transmitter assemblies are each configured to generate a rotating magnetic field. In certain embodiments, the system further comprises a housing assembly and the first and second rotating magnetic field transmitter assemblies are positioned within the housing.

14 Claims, 8 Drawing Sheets

(51) Int. Cl.
*G01D 5/16* (2006.01)
*A61B 5/00* (2006.01)
*A61B 34/20* (2016.01)

(52) U.S. Cl.
CPC ........... *A61B 5/6848* (2013.01); *A61B 5/6851* (2013.01); *A61B 5/6852* (2013.01); *A61B 5/6891* (2013.01); *A61B 5/7228* (2013.01); *A61B 2034/2051* (2016.02)

(56) References Cited

U.S. PATENT DOCUMENTS

| | | |
|---|---|---|
| 5,745,078 A | 4/1998 | Baghdady |
| 6,172,499 B1 | 1/2001 | Ashe |
| 6,537,196 B1 * | 3/2003 | Creighton, IV ... A61B 1/00158 128/897 |
| 2007/0270628 A1 * | 11/2007 | Kawano ............. A61B 1/00158 600/12 |
| 2011/0144479 A1 | 6/2011 | Hastings et al. |
| 2011/0224537 A1 | 9/2011 | Brunner |
| 2011/0248706 A1 | 10/2011 | Davis et al. |

OTHER PUBLICATIONS

International Search Report and Written Opinion issued in PCT/US2018/046803, dated Nov. 14, 2018, 15 pages.

Paperno, E., & Keisar, P. (2004). Three-dimensional magnetic tracking of biaxial sensors. IEEE Transactions on Magnetics, 40(3): 1530-1536.

Song, S., Hu C., Li, B., Li, X., & Meng, M. Q.-H. (2013). An electromagnetic localization and orientation method based on rotating magnetic dipole. IEEE Transactions on Magnetics, 49(3), pp. 1274-1277.

\* cited by examiner

ELECTROMAGNETIC TRACKING SYSTEM USING ROTATING FIELDS GENERATED FROM A RADIAL ARRANGEMENT OF TRANSMITTERS IN A HOUSING

CROSS-REFERENCE TO RELATED APPLICATION

This application claims priority to Provisional Application No. 62/546,532 filed Aug. 16, 2017, which is herein incorporated by reference in its entirety.

TECHNICAL FIELD

The present disclosure relates to systems, methods, and devices for tracking items. More specifically, the disclosure relates to systems, methods, and devices for electro-magnetically tracking medical devices used in medical procedures.

BACKGROUND

A variety of systems, methods, and devices can be used to track medical devices. Tracking systems can use generated magnetic fields that are sensed by at least one tracking sensor in the tracked medical device. The generated magnetic fields provide fixed frame et reference, and the tracking sensor senses the magnetic fields to determine the location and orientation of the sensor in relation to the fixed frame of reference.

SUMMARY

In Example 1, a system comprises first and second rotating magnetic field transmitter assemblies positioned in a planar arrangement. The first and second rotating magnetic field transmitter assemblies are each configured to generate a rotating magnetic field.

In example 2, the system of Example 1, further comprising a housing assembly. The first and second rotating magnetic field transmitter assemblies are positioned within the housing.

In Example 3, the system of any of Examples 1 or 2, wherein the first and second rotating magnetic field transmitter assemblies are each either a coil-based rotating magnetic field transmitter, a permanent-magnet-based rotating magnetic field transmitter, or a coil- and permanent-magnet-based rotating magnetic field transmitter.

In Example 4, the system of any of Examples 1-3, further comprising third, fourth, fifth, and sixth rotating magnetic field transmitter assemblies positioned within a same plane as the first and second rotating magnetic field transmitter assemblies.

In Example 5, the system of any of Examples 1-4, wherein each of the rotating magnetic field transmitter assemblies is energized a frequency different than the other rotating magnetic field transmitter assemblies.

In Example 6, the system of any of Examples 1-5, wherein the rotating magnetic field transmitter assemblies are energized at different times in pairs.

In Example 7, the system of any of Examples 1-8, wherein each of the rotating magnetic field transmitter assemblies is coupled to a respective reference sensor.

In Example 8, the system of any of Examples 1-7, wherein each of the rotating magnetic field transmitter assemblies is a coil-based rotating magnetic field transmitter assembly, and wherein each of the rotating magnetic field transmitter assemblies includes first and second coil windings in an orthogonal arrangement.

In Example 9, the system of any of Examples 1-8, wherein each of the rotating magnetic field transmitter assemblies is a coil-based rotating magnetic field transmitter, and wherein each of the rotating magnetic field transmitter assemblies includes first, second, and third coil windings in an orthogonal arrangement.

In Example 10, the system of any of Examples 8-9, wherein each f the coil windings is wrapped around a shared core.

In Example 11, the system of any of Examples 8-10, wherein each of the first coil windings has a center point and each of the second coil windings has a center point, and wherein the center points are located at a substantially similar position.

In Example 12, the system of any of Examples 1-11, wherein the rotating magnetic field transmitter assemblies are positioned such that the generated rotating magnetic fields overlap each other.

In Example 13, the system of any of Examples 1-12, wherein each of the ting magnetic field transmitter assemblies is either rectangular-shaped or square-shaped.

In Example 14, the system of any of claims 1-13, wherein the rotating magnetic field transmitter assemblies are positioned with respect to each other in a polygonal arrangement.

In Example 15, the system of any of claims 1-14, wherein the rotating magnetic field transmitter assemblies are positioned with respect to each other in a hexagonal arrangement.

In Example 16, a system comprising a housing assembly and first and second rotating magnetic field transmitter assemblies positioned within the housing assembly such that the first and second magnetic field transmitter assemblies are in a planar arrangement. The first an second rotating magnetic field transmitter assemblies are each configured to generate rotating magnetic field.

In Example 17, the system of Example 16, wherein the first and second rotating magnetic field transmitter assemblies are each either a coil-based rotating magnetic field transmitter, a permanent-magnet-based rotating magnetic field transmitter or a coil- and permanent-magnet-based rotating magnetic field transmitter.

In Example 18, the system of Example 18, further comprising third, fourth, fifth, and sixth rotating magnetic field transmitter assemblies positioned within a plane as the first and second rotating magnetic field transmitter assemblies.

In Example 19, the system of Example 18, wherein the first, second, third, fourth, fifth, and sixth rotating magnetic field transmitter assemblies are energized at different times in pairs.

In Example 20, the system of Example 18, wherein each of the rotating magnetic field transmitter assemblies is energized a frequency different than the other rotating magnetic field transmitter assemblies.

In Example 21, the system of Example 18, wherein each of rotating magnetic field transmitter assemblies is energized at different times.

In Example 22, the system of Example 18 wherein the first, second, third, forth fifth, and sixth rotating magnetic field transmitter assemblies are positioned such that the generated rotating magnetic fields overlap each other.

In Example 23, the system of Example 13, wherein the first, second, third, fourth, fifth, and sixth rotating magnetic field transmitter assemblies are positioned with respect to each other within the housing assembly in a polygonal arrangement.

In Example 24, the system of Example 23, wherein the first, second, third, fourth, fifth, and sixth rotating magnetic field transmitter assemblies are positioned with respect to each other within the housing assembly in a hexagonal arrangement.

In Example 25, the system of Example 16, wherein each of the rotating magnetic field transmitter assemblies is coupled to a respective reference sensor.

In Example 26, the system of Example 16, wherein each of the rotating magnetic field transmitter assemblies is a coil-based rotating magnetic field transmitter assembly, and wherein each of the rotating magnetic field transmitter assemblies includes first and second coil windings in an orthogonal arrangement.

In Example 27, the system of Example 26, wherein each of the coil windings is wrapped around a shared core In Example 28, the system of Example 26, wherein each of the first coil windings has a center point and each of the second coil windings has a center point, and wherein the center points are located et a substantially similar position.

In Example 29, the system of Example 16, wherein each of the rotating magnetic field transmitter assemblies is a coil-based rotating magnetic field transmitter, and wherein each of the rotating magnetic field transmitter assemblies includes first, second, and third coil windings in an orthogonal arrangement.

In Example 30, the system of Example 16, wherein each of the rotating magnetic field transmitter assemblies is either rectangular-shaped or square-shaped.

In Example 31 the system of Example 16, wherein the housing assembly comprises fluorotranslucent material.

In Example 32 the system of Example 16, further comprising a magnetic field controller configured to control current applied to the first and second rotating magnetic field transmitter assemblies. The current to be applied to the first rotating magnetic field transmitter assembly is phase shifted from the current to be applied to the second rotating magnetic field transmitter assembly.

In Example 33, the system of Example 16, further comprising a signal processor and a receiver, which is coupled to a medical device. The receiver is configured to sense the rotating magnetic fields and generate a sensed field signal. The signal processor is configured to receive the sensed field signal and to determine location of the receiver.

In Example 34, the system of Example 16, wherein the receiver includes at least one magnetic field sensor comprising one of inductive sensing coils and magnetic sensing elements, wherein the magnetic sensor elements comprise one of magneto-resistive sensing elements.

In Example 35, a system comprising a housing assembly and means for generating a first rotating magnetic field. The means for generating the first rotating magnetic field is positioned within the housing assembly. The system further comprises means for generating a second rotating magnetic field. The means for generating the second rotating magnetic field is positioned within the housing assembly. The means for generating a first rotating magnetic field and the means for generating a second rotating magnetic field are arranged with respect to each other to form a shared magnetic field volume.

In Example 36, the systems of any of Examples 1-32 and 34-35, further comprising a signal processor configured to determine a location of a medical device based on phase and/or amplitude of the generated rotating magnetic fields.

In Example 37, the systems of any of Examples 1-32 and 34-36, further comprising a medical device including a receiver configured to sense the generated rotating magnetic fields.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

While the invention is amenable to various modifications and alternative forms, specific embodiments have been shown by way of example in the drawings and are described in detail below. The intention, however, is not to limit the invention to the particular embodiments described. On the contrary, the invention is intended to cover all modifications, equivalents, and alternatives falling within the scope of the invention as defined by the appended claims.

DETAILED DESCRIPTION

During medical procedures, medical devices such as probes (e.g., catheters) are inserted into a patient. To track the location and orientation of a probe within the patient, probes can be provisioned with magnetic field sensors that detect various magnetic fields generated by transmitters near the patient. For example, transmitters can generate what may be described as rotating magnetic fields. Rotating magnetic field-based tracking can utilize phase-rather than or in addition to amplitude—of the detected fields to determine location and orientation of the probe. Phase-based tracking has certain advantages such as being less sensitive to sensor noise as compared to noise sensitivity of amplitude-based tracking—although phase-based tracking can be used along with amplitude-based tracking. Certain embodiments of the present disclosure are accordingly directed to systems, methods, and devices including magnetic field transmitter assemblies that generate rotating magnetic fields.

Figure 1:
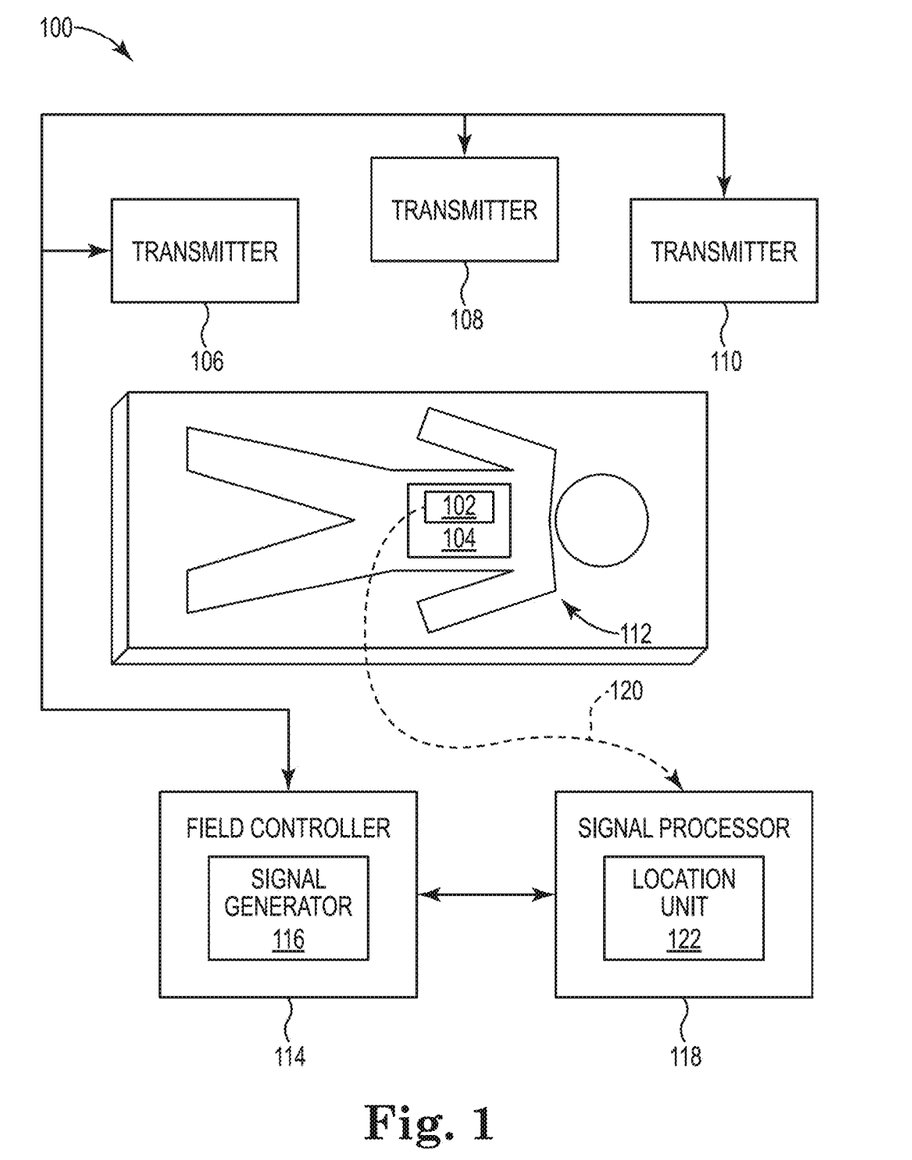
FIG. 1 shows a schematic of a tracking system, in accordance with certain embodiments of the present disclosure.

FIG. 1 is a schematic block diagram depicting a tracking system 100 that is configured to determine location information corresponding to the medical device 104 based on information collected using a receiver (e.g., sensor) 102 associated with a medical device 104. The information collected by the receiver 102 includes a received field signal corresponding to an electromagnetic field defined by a set of electromagnetic signals transmitted by one or more magnetic field transmitter assemblies 106, 108, and 110 (e.g., rotating magnetic field transmitter assemblies). Although only three magnetic field transmitter assemblies are shown, the system 100 can include fewer or more magnetic field transmitter assemblies, as will be described in more detail below. For example, to provide six-degree-of-freedom tracking, the tracking system 100 should include at least one magnetic field transmitter assembly when the receiver 102 includes a three-axis sensor (e.g., three-axis magnetic sensor). Additional magnetic field transmitter assemblies can be used to extend the range and accuracy of tracking. When the receiver 102 includes a dual-axis sensor (e.g., dual-axis magnetic sensor), the tracking system 100 should include at least two magnetic field transmitter assemblies. In embodiments with multiple magnetic field transmitter assemblies, the magnetic field transmitter assemblies can be coupled to a common housing or placed individually. The at least one magnetic field transmitter assembly can be placed under a patient's bed, under the patient but above the patient's bed, and/or placed above the patient (e.g., placed directly on top of the patient or suspended above the patient).

A magnetic field transmitter assembly may be coil-based (e.g., includes one or more coils), permanent-magnet-based (e.g., includes one or more permanent magnets), and/or coil- and permanent-magnet-based—each of which are discussed in more detail below. According to embodiments, one or more magnetic field transmitter assemblies 106, 106, and 110, are configured to transmit (e.g., radiate) electromagnetic signals, which produce a magnetic field (e.g., rotating magnetic field) within which a subject 112 is disposed. According to embodiments, the system 100 includes a magnetic field controller 11 configured to manage operation of the magnetic field transmitter assemblies 106, 108, and 110.

As shown in FIG. 1, the magnetic field controller 114 includes a signal generator 116 configured to provide driving current to each of the magnetic field transmitter assemblies 106, 108, and 110, causing each magnetic field transmitter assembly to transmit an electromagnetic signal. In certain embodiments, the signal generator 116 is configured to provide sinusoidal driving currents to the magnetic field transmitter assemblies 106, 108, and 110. The magnetic field controller 114 can be implemented using firmware, integrated circuits, and/or software modules that interact with each other or are combined together. For example, the magnetic field controller 114 may include computer-readable instructions/code for execution by a processor (see FIG. 2). Such instructions may be stored on a non-transitory computer-readable medium (see FIG. 2) and transferred to the processor for execution. In some embodiments, the magnetic field controller 114 can be implemented in one or more application-specific integrated circuits and/or other forms of circuitry suitable for controlling and processing magnetic tracking signals and information.

The receiver 102 (e.g., magnetic field sensor) (which may include one or more receivers/sensors) may be configured to produce an electrical response to the magnetic field(s) generated by the magnetic field transmitter assemblies 106, 108, and 110. For example, the receiver 102 may include a magnetic field sensor such as inductive sensing coils and/or various sensing elements such as magneto-resistive (MR) sensing elements (e.g., anisotropic magneto-resistive (AMR) sensing elements, giant magneto-resistive (GMR) sensing elements, tunneling magneto-resistive (TMR) sensing elements, Hall effect sensing elements, colossal magneto-resistive (CMR) sensing elements, extraordinary magneto-resistive (EMR) sensing elements, spin Hall sensing elements, and the like), giant magneto-impedance (GMI) sensing elements, and/or flux-gate sensing elements.

The sensed magnetic field signal may include multiple magnetic field signals, each of which may be processed to extract field components corresponding to one or more magnetic field transmitter assemblies. The sensed magnetic field signal is communicated to a signal processor 118, which is configured to analyze the sensed magnetic field signal to determine location information corresponding to the receiver 102 (and, thus, the medical device 104). Location information may include any type of information associated with a location and/or position of a medical device 104 such as, for example, location, relative location (e.g., location relative to another device and/or location), position, orientation, velocity, acceleration, and/or the like. As mentioned above, rotating magnetic field-based tracking can utilize phase (e.g., differences in phase) of the sensed magnetic field signal to determine location and orientation of the probe.

The tracking system 100 can also include at least one sensor that is configured and arranged to sense the magnetic fields generated by the magnetic field transmitter assemblies, 106-110. The sensor can be a magnetic sensor (e.g., dual-axis magnetic sensor, tri-axis magnetic sensor) and be positioned at a known reference point in proximity to the magnetic field transmitter assemblies, 106-110, to act as a reference sensor. For example, one or more sensors can be coupled to the subject's bed, an arm of an x-ray machine, or at other points a known distance from the magnetic field transmitter assemblies, 106-110. In some embodiments, the at least one sensor is mounted to one of the magnetic field transmitter assemblies, 106-110.

The medical device 104 may include, for example, a catheter (e.g., a mapping catheter, an ablation catheter, a diagnostic catheter, an introducer), an endoscopic probe or cannula, an implantable medical device (e.g., a control device, a monitoring device, a pacemaker, an implantable cardioverter defibrillator (ICD), a cardiac resynchronization therapy (CRT) device, a CRT-D), guidewire, endoscope, biopsy needle, ultrasound device, reference patch, robot and/or the like. For example, in embodiments, the medical device 104 may include a mapping catheter associated with an anatomical mapping system. The medical device 104 may include any other type of device configured to be at least temporarily disposed within a subject 112. The subject 112 may be a human, a dog, a pig, and/or any other animal having physiological parameters that can be recorded, or example, ire embodiments, the subject 2 may be a human patient.

As shown in FIG. 1, the medical device 104 may be configured to be disposed within the body of a subject 112, and may be configured to be communicatively coupled to the signal processor 118 via a communication link 120 (shown in phantom). In embodiments, the communication link 120 may be, or include, a wired communication link (e.g., a serial communication), a wireless communication link such as, for example, a short-range radio link, such as Bluetooth, IEEE 802.11, a proprietor), wireless protocol, and/or the like. The term "communication link" may refer to an ability to communicate some type of information in at least one direction between at least two devices, and should not, be understood to be limited to a direct, persistent, or otherwise limited communication channel. That is, in some embodiments, the communication link 120 may be a persistent communication link, an intermittent communication link, an ad-hoc communication link, and/or the like. The communication link 120 may refer to direct communications between the medical device 104 and the signal processor 118, and/or indirect communications that travel between the medical device 104 and the signal processor 118 via at least one other device (e.g., a repeater, router, hub, and/or the like). The communication link 120 may facilitate uni-directional and/or bi-directional communication between the medical device 104 and the signal processor 118. Data and/or co control signals may be transmitted between the medical device 104 and the signal processor 118 to coordinate the functions of the medical device 104 and/or the signal processor 118.

The signal processor 118 further includes a location unit 122 configured to determine, based on the sensed field signal (e.g., the phase, amplitude, differences phase and/or amplitude of the sensed field signal), location information corresponding to the medical device 104. The location unit 122 may be configured to determine location information according to any location-determination technique that uses magnetic navigation. According to various embodiments of the disclosed subject matter, any number of the components depicted in FIG. 1 (e.g., the field controller 114, the signal generator 118, the signal processor 118) may be implemented on one or more computing devices, either as a single unit or a combination of multiple devices. The system 100 can include a display for visualizing the position and/or orientation of the medical device 104 in the subject 112.

Figure 2:
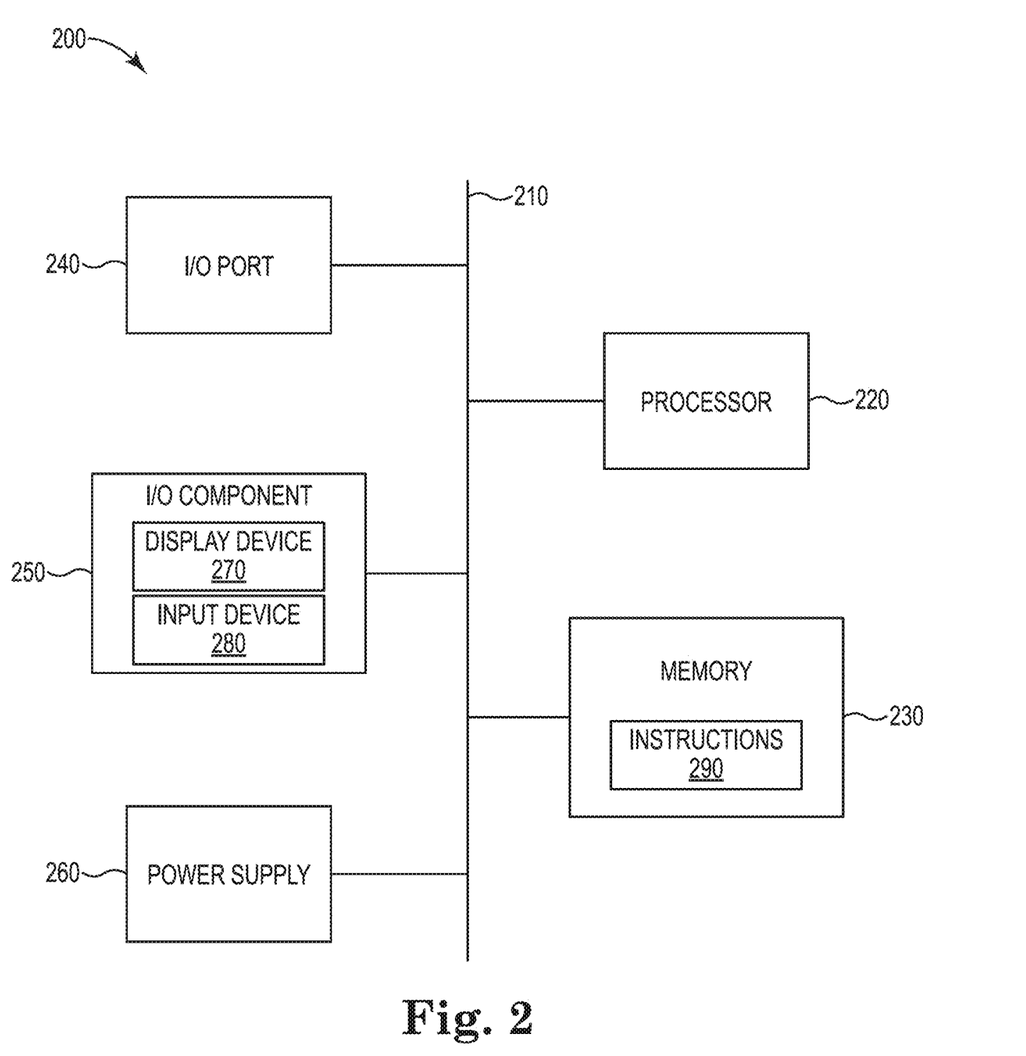
FIG. 2 shows a block representation of a computing device, in accordance with certain embodiments of the present disclosure.

FIG. 2 is a schematic block diagram depicting an illustrative computing device 200, in accordance with embodiments of the disclosure. The computing device 200 may include any type of computing device suitable for implementing aspects of embodiments of the disclosed subject matter. Examples of computing devices include specialized computing devices or general-purpose computing devices such "workstations," "servers," laptops, "desktops," "tablet computers," "hand-held devices," "general-purpose graphics processing units (GPGPUs)," and the like, all of which are contemplated within the scope of FIGS. 1 and 2, with reference to various components of the tracking system 100 and/or computing device 200.

In embodiments, the computing device 200 includes a bus 210 that, directly and/or indirectly, couples the following devices: a processor 220, a memory 230, an input/output (I/O) port 240, an I/O component 250, and a power supply 260. Any number of additional components, different components, and/or combinations of components may also be included in the computing device 200. The I/O component 250 may include a presentation component configured to present information to a user such as, for example, a display device, a speaker, a printing device, and/or the like, and/or an input component such as, for example, a microphone, a joystick, a satellite dish, a scanner, a printer, a wireless device, a keyboard, a pen, a voice input device, a touch input device, a touch-screen device, an interactive display device, a mouse, and/or the like.

The bus 210 represents what may be one or more busses (such as, for example, an address bus, data bus, or combination thereof). Similarly, in embodiments, the computing device 200 may include a number of processors 220, a number of memory components 230, a number of I/O ports 240, a number of I/O components 250, and/or a number of power supplies 260. Additionally any number of these components, or combinations thereof, may be distributed and/or duplicated across a number of computing devices. As an example only, the processor 220 may include the signal processor 118, but other suitable configurations are also contemplated to suit different applications.

In embodiments, the memory 230 includes computer-readable media in the form of volatile and/or nonvolatile memory and may be removable, nonremovable, or a combination thereof. Media examples include Random Access Memory (RAM); Read Only Memory (ROM); Electronically Erasable Programmable Read Only Memory (EEPROM); flash memory; optical or holographic media; magnetic cassettes, magnetic tape, magnetic disk storage or other magnetic storage devices; data transmissions; and/or any other medium that can be used to store information and can be accessed by a computing device such as, for example, quantum state memory, and/or the like. In embodiments, the memory 230 stores computer-executable instructions 290 for causing the processor 220 to implement aspects of embodiments of system components discussed herein and/or to perform aspects of embodiments of methods and procedures discussed herein.

The computer-executable instructions 290 may include, for example, computer code, machine-useable instructions, and the like such as, for example, program components capable of being executed by one or more processors 220 associated with the computing device 200. Program components may be programmed using any number of different programming environments, including various languages, development kits, frameworks, and/or the like. Some or all of the functionality contemplated herein may also, or alternatively, be implemented in hardware and/or firmware.

The illustrative computing device 200 shown in FIG. 2 is not intended to suggest any limitation as to the scope of use or functionality of embodiments of the present disclosure. Neither should the illustrative computing device 200 be interpreted as having any dependency or requirement related to any single component or combination of components illustrated therein. Additionally, various components depicted in FIG. 2 may be, in embodiments, integrated with various ones of the other components depicted therein (and/or components not illustrated), all of which are considered to be within the ambit of the present disclosure.

Figure 3A:
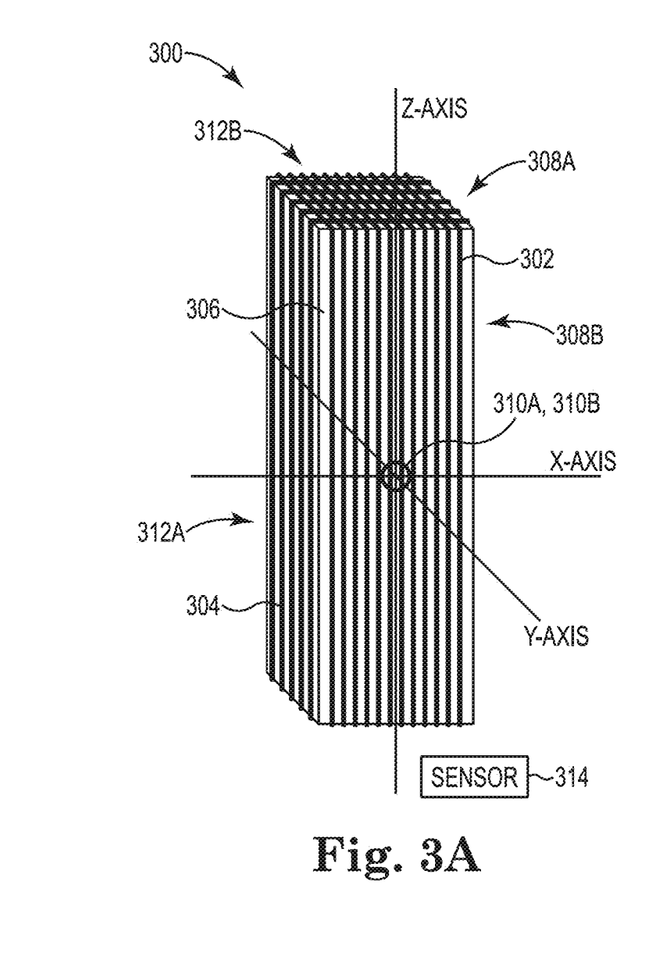
FIGS. 3A-3D show schematics of magnetic field transmitter assemblies, in accordance with certain embodiments of the present disclosure.
Figure 3B:
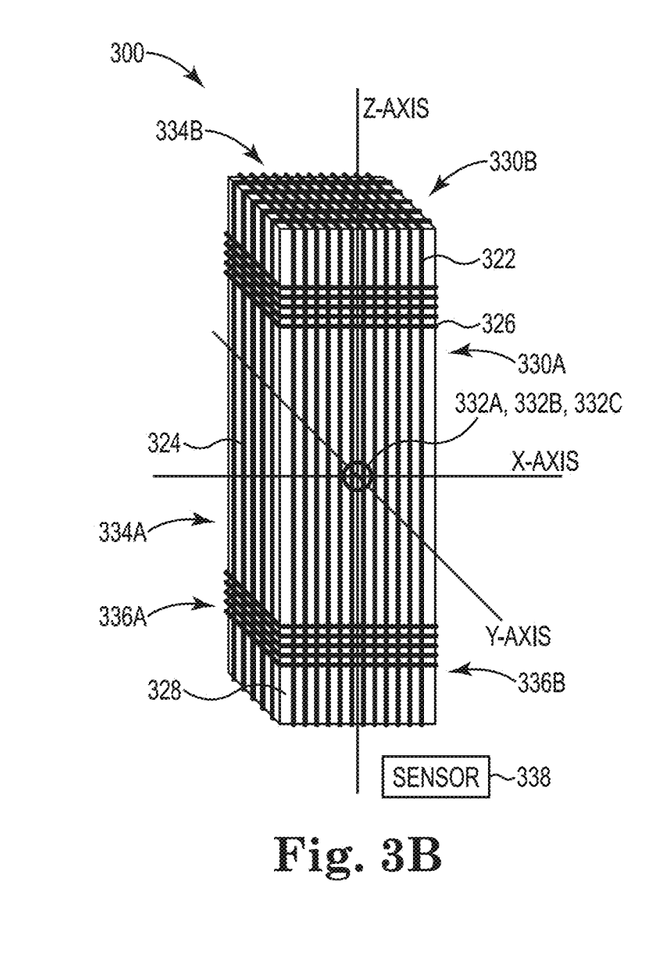
Figure 3C:
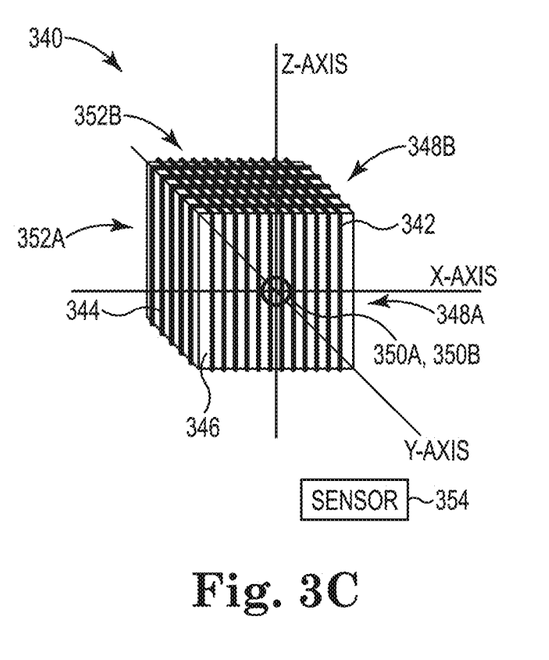
Figure 3D:
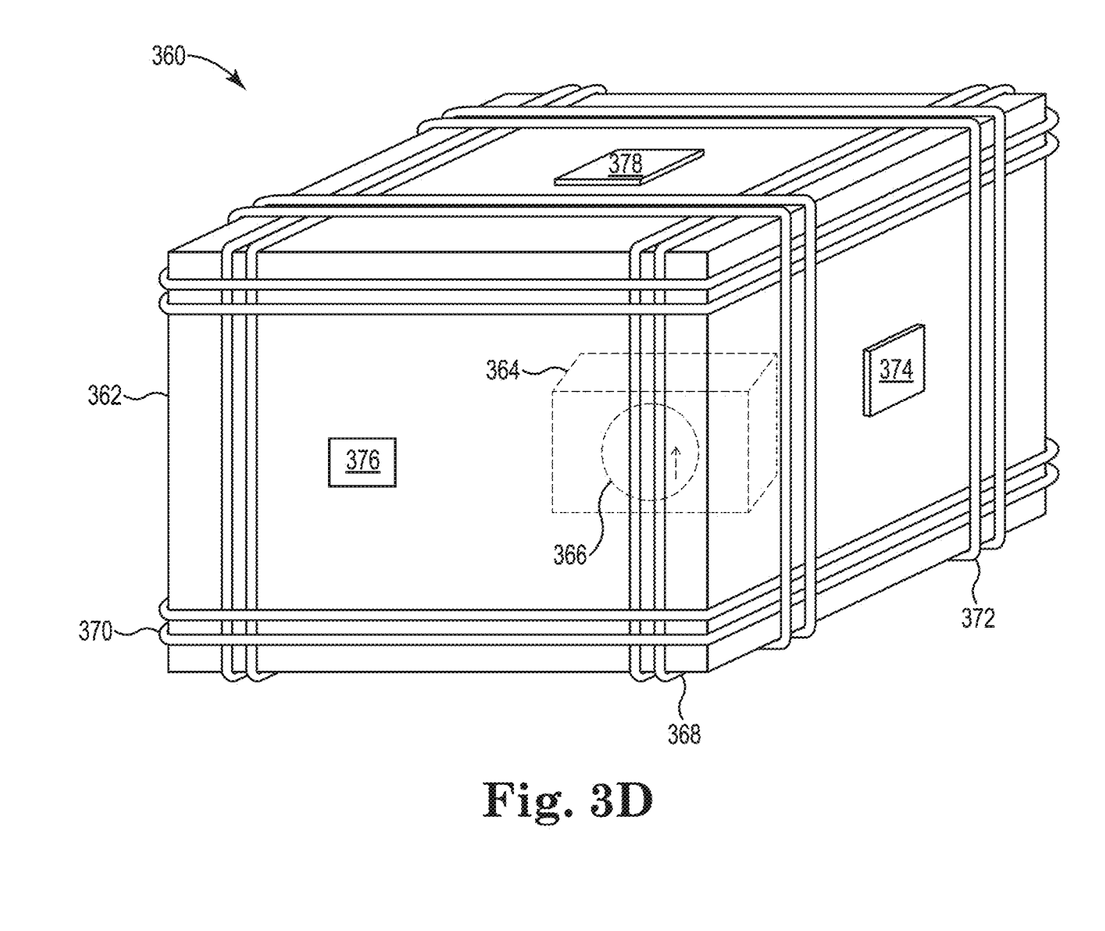

FIGS. 3A-3D show schematics of magnetic field transmitter assemblies (e.g., rotating magnetic field transmitter assemblies) which can be used in the tracking system 100. The magnetic field transmitter assemblies in FIGS. 3A-3C are coil-based and the magnetic field transmitter assembly of FIG. 3D is coil- and permanent-magnet-based.

FIG. 3A shows a magnetic field transmitter assembly 300 rotating magnetic field transmitter assembly) that includes first coil windings 302 and second coil windings 304, which can comprise conductive materials (e.g., copper). For reference, FIG. 3A features an x-axis, a y-axis, and a z-axis. The first coil windings 302 are wrapped around the x-axis and around a core 306. The core 306 can be one of an air core, ferromagnetic material core, and antiferromagnetic material core. As shown, the core 306 is cuboid-shaped such that the first coil windings 302 are substantially rectangular-shaped with four rectangular- or square-shaped external faces of which only two, 308A and 308B are shown in FIG. 3A. The first coil windings 302 are also wrapped around a first center point 310A. The second coil windings 304 are wrapped around the y-axis, the core 306 and a second center point 310B such that the second coil windings 304 are substantially rectangular-shaped with four rectangular- or square-shaped external faces of which only two, 312A and 312B are shown in FIG. 3A. In certain embodiments, the first coil windings 302 overlap the second coil windings 304, or vice versa. In certain embodiments, the first center point 310A and the second center point 310B are positioned at a substantially similar location. Although FIG. 3A shows spacing between windings of the coil windings, the first and second coil windings 302 and 304 can be wound such that the external faces (e.g., 308A-B, 312A-B) of the coil windings fir a wall-like structure comprising windings with little to no spacing between the windings.

As shown in FIG. 3A, the first coil windings 302 and the second coil windings 304 are positioned in an orthogonal arrangement such that the first coil windings 302 and the second coil windings 304 are wound around axes (e.g., x-axis and y-axis) that are substantially orthogonal to each other. Such an arrangement of coil windings can be considered to be a bi-axial orthogonal coil arrangement. As will be discussed in more detail below, when energized (e.g., when current is passed through the coil windings), the magnetic field transmitter assembly 300 generates a magnetic field a rotating magnetic field, cylindrical rotating magnetic field). In some embodiments, the magnetic field transmitter assembly 300 includes or is coupled to or more reference sensors 314, which car comprise one or more of the magnetic field sensors discussed above, including those with Hall effect sensing elements.

FIG. 3B shows a magnetic field transmitter assembly 320 (e.g., rotating magnetic field transmitter assembly) that includes first coil windings 322, second coil windings 324, and third coil windings 326, which can comprise conductive materials (e.g., copper). For reference, FIG. 3B features an x-axis, a y-axis, and a z-axis. The first coil windings 322 are wrapped around the x-axis and around a core 328. The core 328 can be one of an air core, ferromagnetic material core, and antiferromagnetic material core. As shown, the core 328 is cuboid-shaped such that the first coil windings 322 are substantial y rectangular-shaped with four rectangular- or square-shaped external faces of which only two, 330A and 330B are shown in FIG. 3B. The first coil windings 322 are also wrapped around a first center point 332A. The second coil windings 324 are wrapped around the y-axis, the core 328, and a second center point 332B such that the second coil windings 324 are substantially rectangular-shaped with four rectangular- or square-shaped external faces of which only two, 334A and 334B are shown in FIG. 3B. The third coil windings 328 are wrapped around the z-axis, the core 328, and a third center point 332C such that the third coil windings 326 are substantially rectangular-shaped or square-shaped with four rectangular- or amore-shaped external faces of which only two, 336A and 336B are shown in FIG. 3B.

In certain embodiments, the first coil windings 322, the second coil windings 324, and the third coil windings 326 are layered such that some coil windings overlap others. In certain embodiments, the first center point 330A, the second center point 310B, and/or the third center point 330C are positioned at a substantially similar location. Although FIG. 3B shows spacing between windings of the coil windings, the first, second, and third coil windings 322, 324, and 326 can be wound such that the external faces (e.g., 330A-B, 334A-B, 336A-B) of the coil windings form a wall-like structure comprising windings with little to no spacing between the windings.

As shown in FIG. 3B, the first coil windings 322, the second coil windings 324, and the third coil windings 326 are positioned in an orthogonal arrangement such that the first coil windings 322, the second coil windings 324, and the third coil windings 326 are wound around axes (e.g., x-axis, y-axis, and z-axis) that are substantially orthogonal to each other. Such air arrangement of coil windings can be considered to be a tri-axial orthogonal coil arrangement. As will is used in detail below, when energized (e.g., when current is passed through the coil windings), the magnetic field transmitter assembly 320 generates a magnetic field (e.g., a rotating magnetic field, cylindrical rotating magnetic field). In some embodiments, the magnetic field transmitter assembly 320 includes or is coupled to one or more reference sensors 340, which can comprise one or more of the magnetic field sensors discussed above, including those with Hall effect sensing elements.

FIG. 3C shows a magnetic field transmitter assembly 340 (e.g., rotating magnetic field transmitter assembly) that includes first coil windings 342 and second coil windings 344, which can comprise conductive materials (e.g., copper). For reference, FIG. 3C features an x-axis, a y-axis, and a z-axis. The first coil, windings 342 are rapped around the x-axis and around a core 346. The core 346 can be one of an air core, ferromagnetic material core, and antiferromagnetic material core. As shown, the core 356 is cube-shaped such that the first coil windings 342 are substantially square-shaped with four square-shaped external faces of which only two, 348A and 348B are shown in FIG. 3C. The first coil windings 342 are also wrapped around a first center point 350A. The second coil windings 344 are wrapped around the y-axis, the core 356, and a second center point 350B such that the second coil windings 344 are substantially square-shaped with four square-shaped external faces of which only two, 352A and 352B are shown in FIG. 3C. In certain embodiments, the coil windings overlap the second coil windings 344, or vice versa. In certain embodiments, the first center point 350A and the second center point 350B are positioned at a substantially similar location. Although FIG. 3C shows spacing between windings of the coil windings, the first and second coil windings 342 and 344 can be wound such that the external faces (e.g., 346A-B, 352A-B) of the coil windings form a wall-like structure comprising windings with little to no spacing between the windings.

As shown in FIG. 3C, the first coil windings 342 and the second coil windings 344 are positioned in an orthogonal arrangement such that the first c windings 342 and the second coil windings 344 are wound around axes (e.g., x-axis and y-axis) that are substantially orthogonal to each other. Such an arrangement of coil windings can be considered to be a cube-shaped bi-axial orthogonal coil arrangement. As will be discussed in more detail below, when energized (e.g., when current is passed through the coil windings), the magnetic field transmitter assembly 340 generates a magnetic field (e.g., a rotating magnetic field, cylindrical rotating magnetic field). In some embodiments, the magnetic field transmitter assembly 340 includes or is coupled to one or more reference sensors 354, which can comprise one or more of the magnetic field sensors discussed above, including those with Hall effect sensing elements.

FIG. 3D shows a schematic of a magnetic field transmitter assembly 360 including an enclosure 362, a subassembly 364 (in dotted lines), a magnet 366 (in dotted lines), a first set of coils 368, second set of coils 370, a third set of coils 372, a first magnetic field sensor 374, a second magnetic field sensor 376, and a third magnetic field sensor 378. Each set of coils can be comprised of a single wire with multiple coil turns around the enclosure 362. The coils can be comprised of conductive materials such as copper. When energized, the first set of coils 368, the second set of coils 370, and the third set of coils 372 generate magnetic fields that can be controlled to rotate the permanent magnet 366 within the subassembly 364.

The first set of coils 388, the second set of coils 370, and the third set of coils 37 rare wrapped around the enclosure 362, which houses the subassembly 364 and the magnet 386. Although the enclosure 382 is shown as being cube shaped, the enclosure 382 can be other shapes (e.g., cuboid, sphere, ellipsoid, cylindrical). For simplicity, only a few coil turns are shown as being included in the first set of coils 368, the second set of coils 370, and the third set of coils 372, but each set of coils can include many coils turns. In some embodiments, the sets of coils are wrapped such that the coils substantially cover the enclosure 382. In some embodiments, the sets of coils are wrapped orthogonally with respect to each other. In some embodiments, each set of coils is wrapped in a Helmholtz coil arrangement, which can be referred to as a 3-axis Helmholtz arrangement. For example, as shown in FIG. 3D, each set of coils includes subsets of coil windings at ends (e.g., near vertices) of the enclosure 362 that are separated by an area without coil windings. Helmholtz coils may provide a more uniform magnetic field within a volume of the enclosure 362 compared to a magnetic field generated by sets of a single, continuous coils covering faces of the enclosure 362.

The magnet 366 can comprise various magnetic materials such a Nd, Fe, Co, Sm, and the like. For example, the magnet 366 can comprise permanent magnetic materials such as NdFeB, SmCo, and the like. In some embodiments, the magnet 366 includes a coating that is coated around the permanent magnetic materials and that has a low coefficient of friction and/or high resistance to wear. For example, the coating include metal plating (e.g., Ni) surrounding the permanent magnetic materials. In certain embodiments, the magnet 366 is coated with a low-friction plastic material such as polyoxymethylene or polytetrafluoroethylene. The magnet 366 can be a dipole, have a preferred magnetic orientation (represented by an arrow), and have a uniform magnetization throughout the permanent magnetic material within the magnet 306. In embodiments, the magnet 366 is sphere shaped and has a diameter of 0.25" to in some embodiments, the magnet 366 has a diameter of 0.25" to 1".

The magnet 366 can be positioned in the subassembly 364, which can form a clam-shell-like enclosure around the magnet 366. The subassembly 364 and the enclosure 362 can comprise non-magnetic materials with low coefficients of friction (e.g., polytetrafluoroethylenes, ceramics). In certain embodiments, the subassembly 364 comprises materials having a low coefficient of friction with respect to the coating of the magnet 366. A lubricant (e.g., oils, waxes, silicone, graphite, fluoropolymers) can be applied to internal surface of the subassembly 364 to reduce friction between the internal surfaces and the magnet 366.

During operation, the magnetic field transmitter assembly 360 may be configured to generate a rotating magnetic field. The rotating magnetic field is generated by rotating the magnet 366. The magnet 366 is rotated by applying and controlling current applied to the coils surrounding the enclosure 362. The applied current generates a magnetic field that, when controlled, causes the magnet 366 to rotate via a controlled torque.

The first magnetic field sensor 374, the second magnetic field sensor 376, and the third magnetic field sensor 378 can be coupled to the enclosure 362 and be configured to sense the rotating magnetic field generated by the magnet 366. The first magnetic field sensor 374, the second magnetic field sensor 376, and the third magnetic field sensor 378 can include inductive sensing coils and/or various sensing elements such as MR sensing elements (e.g., AMR sensing elements, GMR sensing element TMR sensing elements, Hall effect sensing elements, CMR sensing elements, EMR sensing elements, spin Hall sensing elements, and the like), GMI sensing elements, and/or flux-gate sensing elements.

A magnetic field controller (such as the magnetic field controller 114 of FIG. 1) can be configured to control current to the magnetic field transmitter assembly 360. As described above, during operation, the magnetic field transmitter assembly 360 is configured to generate a rotating magnetic field by rotating the magnet 366 by applying and controlling current applied to the coils surrounding the magnet 366. The applied current generates a magnetic field that causes the magnet to rotate via torque. The magnetic field controller is configured to apply current to the first set of coils 368, the second set of coils 370, and the third set of coils 372, which can be wrapped orthogonal to each other such that the first set of coils 368 is considered to be a x-axis coil, the second set of coils 370 is considered to be a y-axis coil, and the third set of coils 372 is considered to be a z-axis coil. The first magnetic field sensor 374 is positioned to sense x-axis-components of the rotating magnetic field, the second magnetic field sensor 376 is positioned to sense y-axis-components of the rotating magnetic field, and the third magnetic field sensor 378 is positioned to sense z-axis-components of the rotating magnetic field. The magnetic fields sensed by the x-axis magnetic field sensor (i.e., first sensor 374) are used as input to the magnetic field controller to determine an amount of current to be applied to the y-axis coil (i.e., the second set of coils 370). Similarly, the magnetic fields sensed by the y-axis magnetic field sensor (i.e., second sensor 376) are used as input to the magnetic field controller to determine an amount of current to be applied to the z-axis coil (i.e., the third set of oils 372). And, the magnetic fields sensed by the z-axis magnetic field sensor (i.e., third sensor 378) are used as input to the magnetic field controller 500 to determine an amount of current to be applied to the x-axis coil (i.e., the first set of coils 368).

Figure 4A:
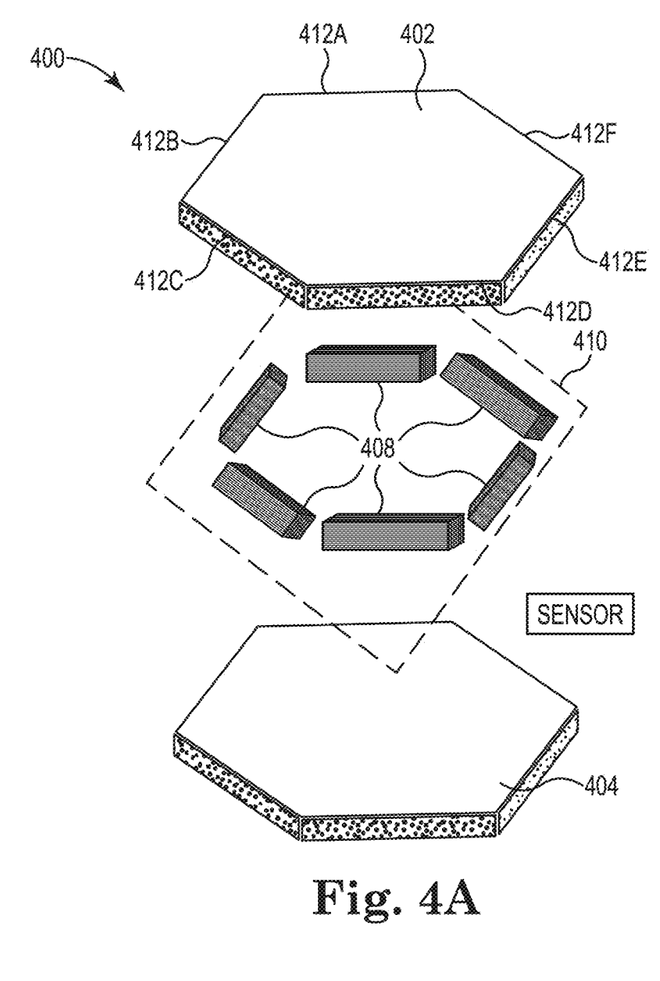
FIG. 4A shows an exploded, perspective view of a schematic housing assembly, in accordance with certain embodiments of the present disclosure.
Figure 4B:
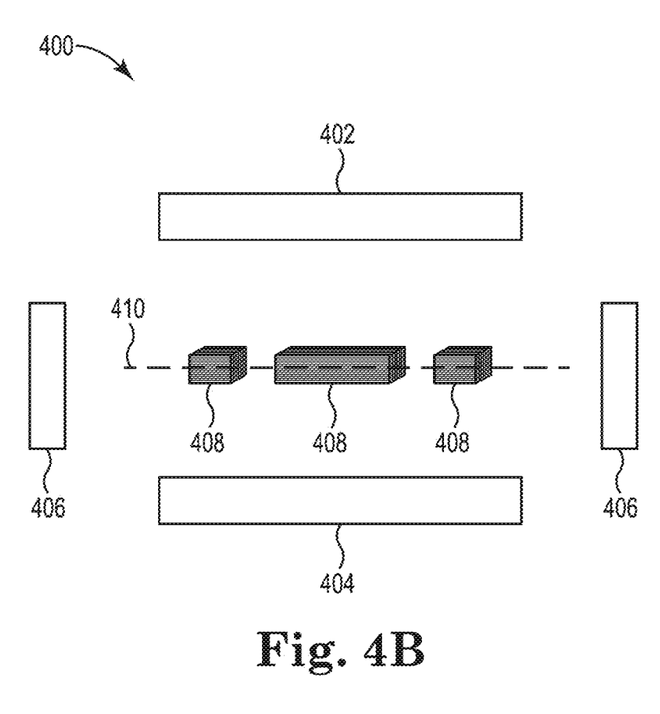
FIG. 4B shows an exploded, side view of the housing assembly of FIG. 4A.

FIGS. 4A and 4B show exploded views of a housing assembly 400 including a top portion 402, bottom portion 404, side ells 406, and one or more magnetic field transmitter assemblies 408 (e.g., rotating magnetic field transmitter assemblies). When the housing assembly 400 is assembled, the magnetic field transmitter assemblies 408 are positioned within the housing assembly 400. In certain embodiments, the top portion 402 and/or the bottom portion 404 form the sidewalls 406.

FIGS. 4A and 4B show a plane 410 in which each of the magnetic field transmitter assemblies 408 are positioned along. When positioned along the same plane 410, the magnetic field transmitter assemblies 408 can be considered to be in a planar arrangement. As shown in FIG. 4A, the magnetic field transmitter assemblies 408 are positioned with respect to each other in a hexagonal arrangement. For example, each magnetic field transmitter assembly 408 is positioned along and substantially parallel to one of the six sides, 412A-412F of the hexagonal-shaped housing assembly 400. In some embodiments, one or more of the magnetic field transmitter assemblies 408 can be positioned at vertices of the hexagonal-shaped housing assembly 400. As will be shown below, the housing assembly 400 can be other shapes, including but limited to other polygonal shapes, circular shapes, donut shapes, and/or the like. The housing assembly 400 can comprise various materials such as fiberglass, carbon fiber, phenolics, and other materials that can be made to be structurally rigid and fluorotransparent. Various components of the housing assembly 400 can be assembled together using non-metal materials and/or fasteners (e.g., plastic fasteners like clips and screws, epoxies). In some embodiments, the housing assembly 400 is formed using one or more molds.

The magnetic field transmitter assemblies 408 can include magnetic field transmitter assemblies like those shown in FIGS. 3A-D (e.g., magnetic field transmitter assemblies 300, 320, 340, and 360). As mentioned above, the magnetic field transmitter assemblies 408 are configured to generate a magnetic field. In certain embodiments, the magnetic field transmitter assemblies 408 are configured to generate a rotating magnetic field. Rotating magnetic field-based tracking can utilize phase of the detected rotating magnetic fields to determine location and orientation of a probe (e.g., medical device 104 of FIG. 1). Example field zones of rotating magnetic fields generated by magnetic field transmitter assemblies 300, 320, 340, and 360 are shown in FIGS. 5A and 5B.

Figure 5A:
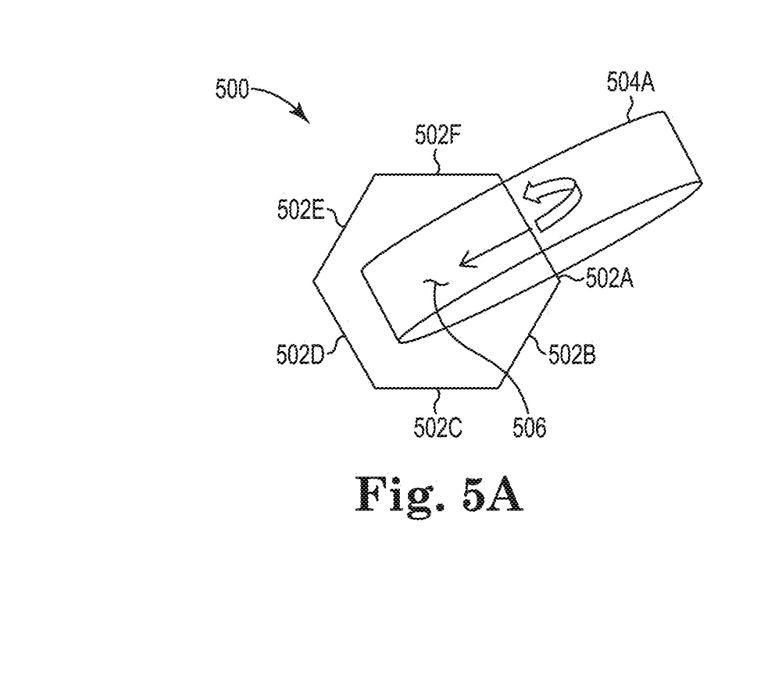
FIGS. 5A and 5B show schematics of an arrangement of magnetic field transmitter assemblies and magnetic fields, in accordance with certain embodiments of the present disclosure.
Figure 5B:
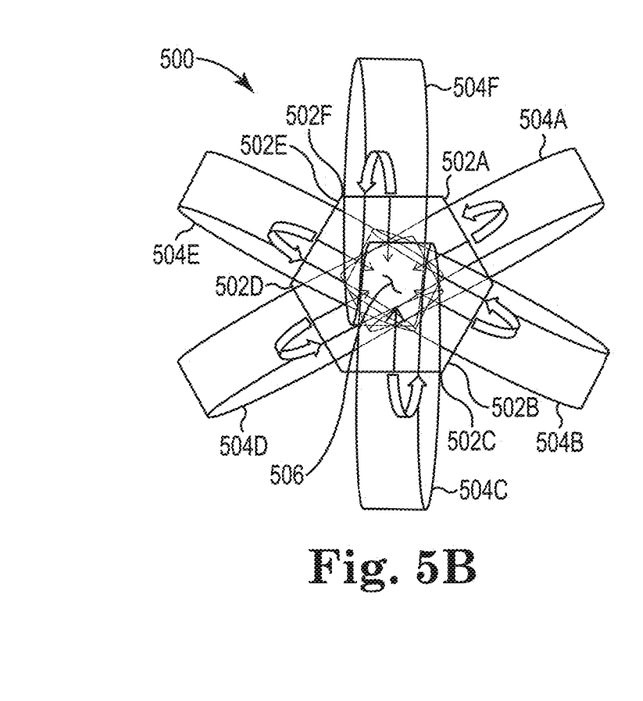

FIG. 5A shows a schematic of a hexagonal arrangement 500 of magnetic field transmitter assemblies 502A-F (e.g., rotating magnetic field transmitter assemblies) and an example magnetic field 504A generated by one of the magnetic field transmitter assemblies 502A. FIG. 5B shows the arrangement 500 of magnetic field transmitter assemblies 502A-F and example magnetic fields 504A-F generated by each of the magnetic field transmitter assemblies 502A-F. Each magnetic field transmitter assembly is represented by a side of the hexagonal arrangement 500.

When energized (e.g., when current is passed through the coil winding of the magnetic field transmitter assembly), each magnetic field transmitter assembly 502A-F is configured to generate a magnetic field. FIGS. 5A and 5B show magnetic fields 504A-F that can be characterized as rotating magnetic fields, and more specifically, cylindrical rotating magnetic fields. In FIGS. 5A and 5B, the rotating magnetic fields, 504A-F, are represented by cylinder-shaped fields that each rotate around a respective axis (E.g., longitudinal axis, z-axis of magnetic field transmitter assemblies 300, 320, and 34) of one of the magnetic field transmitter assemblies 502A-F. As shown in FIG. 5B, a portion of each of the rotating magnetic fields, 504A-F, overlap each other in a shared magnetic field volume 506 of the hexagonal arrangement 500 of magnetic field transmitter assemblies 502A-F. In certain embodiments, the shared magnetic field volume 506 is centrally located within the hexagonal arrangement 500. The shared magnetic field volume 506 should be positioned where the receiver/sensor (e.g., receiver 102 in FIG. 1) and to-be-tracked medical device (e.g., medical device 104 in FIG. 1) is be likely positioned during a procedure. For example, the hexagonal arrangement 500 of magnetic field transmitter assemblies 502A-F (via positioning of a housing assembly, such as housing assembly 400 of FIGS. 4A and 4B) can be positioned such that the shared magnetic field volume 506 covers a patient's heart and/or lung. In some embodiments, the hexagonal arrangement 500 (via positioning of a housing assembly) is positioned above a patient, below a patient but above an operating table, below a patient and below an operating table, or is positioned and shaped to surround a patient.

The rotating magnetic fields 504A-F are generated by applying current at particular frequencies and/or at particular time intervals. Using the magnetic field transmitter assembly 300 of FIG. 3A as an example, the rotating magnetic field 504A shown in FIG. 5A can be generated by applying current to the first coil windings 302 and second coil windings 304. In certain embodiments, current applied to the first coil windings 302 and the second coil windings 304 are phase shifted from each other. For example, the current applied to the first coil windings 302 can be a sine-wave-based current, and the current applied to the second coil windings 304 can be a cosine-wave-based current. These currents have phases that are shifted approximately 90 degrees from each other. The particular current applied to the coil windings in the magnetic field transmitter assemblies can be determined by one or more controllers and signal generators such as the magnetic field controller 114 and the signal generator 116 shown in FIG. 1.

In certain embodiments, the magnetic field transmitter assemblies 502A-F are energized sequential one at a time. For example, as shown in FIG. 5A, only the magnetic field transmitter assembly 502A is energized and only one rotating magnetic field 504A has been generated. After the magnetic field transmitter assembly 502A has been energized, another magnetic field transmitter assembly (e.g., 502B) can be energized followed by 504C, 504D, 504E, and then 504F after which 504A is energized again. This sequential energizing can be considered to be a timing based multiplexing approach. Another timing-based multiplexing approach involves simultaneously energizing pairs of the magnetic field transmitter assemblies 502A-F. For example, magnetic field transmitter assemblies, 504A and 504D, can be energized simultaneously followed by another pair, 504B and 504E, followed by another pair, 504C and 504F. When using a timing-based multiplexing approach, each magnetic field transmitter assembly can be energized multiple times per second (e.g., 20 times/second, 40 times/second, 60 times/second). In certain embodiments, the current applied to each magnetic field transmitter assembly or pair of assemblies has a different frequency. The current frequencies can be 500 Hz to 10 kHz, 500 Hz to 30 kHz, for example, and can differ between magnetic field transmitter assemblies by approximately 25 Hz to 1 kHz (e.g., 50 Hz, 100 Hz, 500 Hz, and 1 kHz). For example, one magnetic field transmitter assembly 504A may be energized by a current at a frequency of 600 Hz while another magnetic field transmitter assembly 504B may be energized by current at 840 Hz while another magnetic field transmitter assembly 504C may be energized by current at 880 Hz. In this example, the magnetic field transmitter assemblies are energized by currents that differ in frequency by 40 Hz.

In certain embodiments, as shown in FIG. 5B, the magnetic field transmitter assemblies 502A-F can be energized simultaneously and at different frequencies. Energizing the magnetic field transmitter assemblies 502A-F at different frequencies can be considered to be a frequency-based multiplexing approach. The rent frequencies can be 500 Hz to 10 kHz, 500 Hz to 30 kHz, for example, and can differ between magnetic field transmitter assemblies by approximately 25 Hz to 1 kHz (e.g., 50 Hz, 100 Hz, 500 Hz, and 1 kHz). For example, one magnetic field transmitter assembly 504A may be energized by a current at a frequency of 800 Hz while another magnetic field transmitter assembly 504B may be energized by current at 840 Hz while another magnetic field transmitter assembly 504C may be energized by current at 880 Hz. In this example, the magnetic field transmitter assemblies are energized by currents that differ in frequency by 40 Hz.

FIGS. 6A-6D show top view schematics of various housing assemblies and arrangements of magnetic field transmitter assemblies. Like the housing assemblies and arrangements discussed above, the housing assemblies and arrangements shown in FIGS. 6A-D include magnetic field transmitter assemblies that are positioned with the housing assemblies and that are configured to generate magnetic fields (e.g., rotating magnetic fields). The magnetic field transmitter assemblies can be arranged such that they create a shared magnetic field volume. Further, in each of the arrangements shown in FIGS. 6A-6D, the magnetic field transmitter assemblies can be positioned along a single plane (e.g., a planar arrangement). The rotating, magnetic fields can be sensed and analyzed to determine location information corresponding to the receiver/sensor 102 (and, thus, the medical device 104). Likewise, the housing assemblies and arrangements shown in FIGS. 6A-D can be used or incorporated into systems such as the tracking system 100.

Figure 6A:
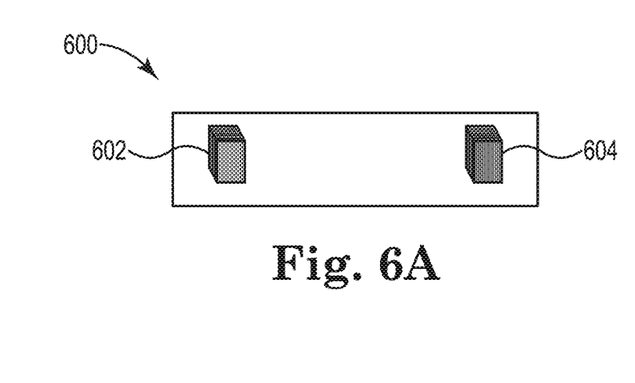
FIGS. 6A-6D show top view schematics of various housing assemblies and arrangements of magnetic field transmitter assemblies, in accordance with certain embodiments of the present disclosure.

The housing assembly 800 shown in FIG. 6A includes two magnetic field transmitter assemblies (i.e., a first magnetic field transmitter assembly 602 and a second magnetic field transmitter assembly 604). The housing assembly 600 is rectangular shaped with the first magnetic field transmitter assembly 602 and the second magnetic field transmitter assembly 604 positioned at opposite ends of the housing assembly 600. Although the first magnetic field transmitter assembly 602 and the second magnetic field transmitter assembly 604 are shown as square-shaped assemblies like the magnetic field transmitter assembly 360 of FIG. 3C, the housing assembly 600 can include magnetic field transmitter assemblies that are rectangular shaped, are permanent-magnet-based, are bi- or tri-axial orthogonal coil arrangements, etc. Although only two magnetic field transmitter assemblies are shown in the rectangular-shaped housing assembly 600, the rectangular-shaped housing assembly 600 can include additional magnetic field transmitter assemblies.

Figure 6B:
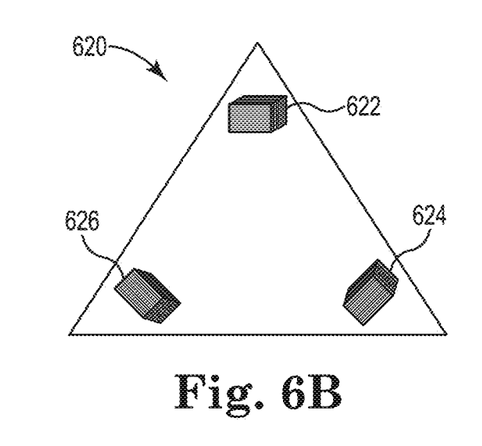

The housing assembly 620 shown in FIG. 6B includes three magnetic field transmitter assemblies (i.e., a first magnetic field transmitter assembly 622, a second magnetic field transmitter assembly 624, and a third magnetic field transmitter assembly 626). The housing assembly 620 is triangular shaped with the first magnetic field transmitter assembly 622, the second magnetic field transmitter assembly 624, and the third magnetic field transmitter assembly 626 positioned at vertices of the triangular-shaped housing assembly 620. Although the first magnetic field transmitter assembly 622, the second magnetic field transmitter assembly 624, and the third magnetic field transmitter assembly 626 are shown as square-shaped assemblies like the magnetic field transmitter assembly 360 of FIG. 3C, the housing assembly 620 can include magnetic field transmitter assemblies that are rectangular shaped, are permanent-magnet-based, are bi- or tri-axial orthogonal coil arrangements, etc. Although only three magnetic field transmitter assemblies are shown in the triangular-shaped housing assembly 620, the triangular-shaped housing assembly 620 can include additional magnetic field transmitter assemblies and/or magnetic field transmitter assemblies that are positioned at different points within the triangular-shaped housing assembly 620.

Figure 6C:
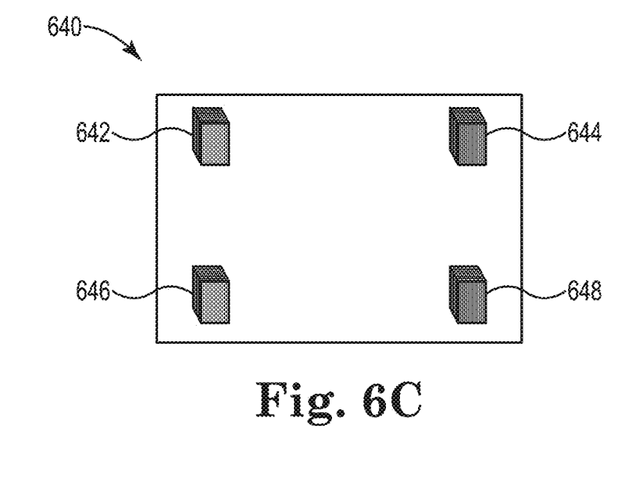

The housing assembly 640 shown in FIG. 6C includes four magnetic field transmitter assemblies (i.e., a first magnetic field transmitter assembly 642, a second magnetic field transmitter assembly 644, a third magnetic field transmitter assembly 646, and a fourth magnetic field transmitter assembly 648). The housing assembly 640 is square shaped with the first magnetic field transmitter assembly 642, the second magnetic field transmitter assembly 644, the third magnetic field transmitter assembly 646, and the fourth magnetic field transmitter assembly 648 positioned at corners of the square-shaped housing assembly 640. Although the first magnetic field transmitter assembly 642, the second magnetic field transmitter assembly 644, the third magnetic field transmitter assembly 646, and the fourth magnetic field transmitter assembly 648 are shown as square-shaped assemblies like the magnetic field transmitter assembly 360 of FIG. 3C, the housing assembly 640 can include magnetic field transmitter assemblies that are rectangular shaped, are permanent-magnet-based, are bi- or tri-axial orthogonal coil arrangements, etc. Although only four magnetic field transmitter assemblies are shown in the square-shaped housing assembly 640, the square-shaped housing assembly 640 can include additional magnetic field transmitter assemblies and/or magnetic field transmitter assemblies that are positioned at different points within the square-shaped housing assembly 640.

Figure 6D:
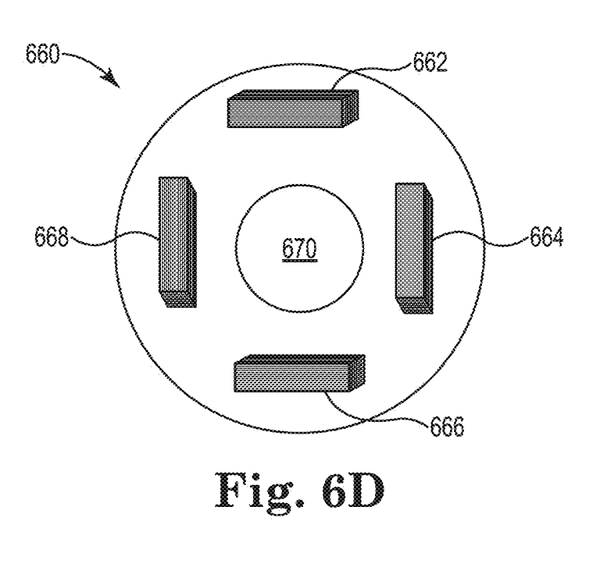

The housing assembly 660 shown in FIG. 6D includes four magnetic field transmitter assemblies (i.e., a first magnetic field transmitter assembly 662, a second magnetic field transmitter assembly 664, a third magnetic field transmitter assembly 666, and a fourth magnetic field transmitter assembly 668). The housing assembly 660 is donut shaped with the first magnetic field transmitter assembly 662, the second magnetic field transmitter assembly 665, the third magnetic field transmitter assembly 666, and the fourth magnetic field transmitter assembly 668 in a square- or rectangular-shaped arrangement around a central opening 670 in the housing assembly 660. Although the first magnetic field transmitter assembly 662, the second magnetic field transmitter assembly 664, the third magnetic field transmitter assembly 666, and the fourth magnetic field transmitter assembly 648 are shown as rectangular-shaped assemblies like the magnetic field transmitter assembly 300 of FIG. 3A, the housing assembly 660 can include magnetic field transmitter assemblies that are rectangle shaped, are permanent-magnet-based, are bi- or tri-axial orthogonal coil arrangements, etc. Although only four magnetic field transmitter assemblies are shown in the donut-shaped housing assembly 660, the donut-shaped housing assembly 660 can include additional magnetic field transmitter assemblies and/or magnetic field transmitter assemblies that are positioned at different points within the donut-shaped housing assembly 660.

Various modifications and additions can be made to the exemplary embodiments discussed without departing from the scope of the present invention. For example, while the embodiments described above refer to particular features, the scope of this invention also includes embodiments having different combinations of features and embodiments that do not include all of the described features. Accordingly, the scope of the present invention is intended to embrace all such alternatives, modifications, and variations as fall within the scope of the claims, together with all equivalents thereof.

We claim:

1. A system comprising:
    a housing assembly;
    first and second rotating magnetic field transmitter assemblies positioned within the housing assembly such that the first and second magnetic field transmitter assemblies are in a planar arrangement, wherein the first and second rotating magnetic field transmitter assemblies are each configured to generate a rotating magnetic field; and
    third, fourth, fifth, and sixth rotating magnetic field transmitter assemblies positioned within a same plane as the first and second rotating magnetic field transmitter assemblies;
    wherein the first, second, third, fourth, fifth, and sixth rotating magnetic field transmitter assemblies are energized at different times in pairs;
    wherein each of the rotating magnetic field transmitter assemblies is a coil-based rotating magnetic field transmitter assembly, and wherein each of the rotating magnetic field transmitter assemblies includes first and second coil windings in an orthogonal arrangement.

2. The system of claim 1, wherein the first and second rotating magnetic field transmitter assemblies are each either a coil-based rotating magnetic field transmitter, a permanent-magnet-based rotating magnetic field transmitter, or a coil- and permanent-magnet-based rotating magnetic field transmitter.

3. The system of claim 1, wherein each of the rotating magnetic field transmitter assemblies is energized at a frequency different than the other rotating magnetic field transmitter assemblies.

4. The system of claim 1, wherein the first, second, third, fourth, fifth, and sixth rotating magnetic field transmitter assemblies are positioned such that the generated rotating magnetic fields overlap each other.

5. The system of claim 1, wherein the first, second, third, fourth, fifth, and sixth rotating magnetic field transmitter assemblies are positioned with respect to each other within the housing assembly in a polygonal arrangement.

6. The system of claim 5, wherein the first, second, third, fourth, fifth, and sixth rotating magnetic field transmitter assemblies are positioned with respect to each other within the housing assembly in a hexagonal arrangement.

7. The system of claim 1, wherein each of the rotating magnetic field transmitter assemblies is coupled to a respective reference sensor.

8. The system of claim 1, wherein each of the coil windings is wrapped around a shared core.

9. The system of claim 1, wherein each of the first coil windings has a center point and each of the second coil windings has a center point, and wherein the center points are located at a similar position.

10. The system of claim 1, wherein each of the rotating magnetic field transmitter assemblies is either rectangular-shaped or square-shaped.

11. The system of claim 1, further comprising:
a magnetic field controller configured to control current applied to the first and second rotating magnetic field transmitter assemblies, wherein the current to be applied to the first rotating magnetic field transmitter assembly is phase shifted from the current to be applied to the second rotating magnetic field transmitter assembly.

12. The system of claim 1, further comprising:
a receiver coupled to a medical device, the receiver configured to sense the rotating magnetic fields and generate one or more sensed field signals; and
a signal processor configured to receive the sensed field signal and to determine location of the receiver based on a phase of the one or more sensed field signals.

13. The system of claim 1, wherein the receiver includes at least one magnetic field sensor comprising one of inductive sensing coils and magnetic sensing elements, wherein the at least one magnetic field sensor comprises one of magneto-resistive sensing elements.

14. A system comprising:
a housing assembly;
first and second rotating magnetic field transmitter assemblies positioned within the housing assembly such that the first and second magnetic field transmitter assemblies are in a planar arrangement, wherein the first and second rotating magnetic field transmitter assemblies are each configured to generate a rotating magnetic field; and
third, fourth, fifth, and sixth rotating magnetic field transmitter assemblies positioned within a same plane as the first and second rotating magnetic field transmitter assemblies;
wherein the first, second, third, fourth, fifth, and sixth rotating magnetic field transmitter assemblies are energized at different times in pairs;
wherein each of the rotating magnetic field transmitter assemblies is a coil-based rotating magnetic field transmitter, and wherein each of the rotating magnetic field transmitter assemblies includes first, second, and third coil windings in an orthogonal arrangement.

* * * * *